United States Patent [19]

Moore

[11] 4,274,978
[45] Jun. 23, 1981

[54] STANDARDS FOR DETERMINING GLYCOSYLATED HEMOGLOBIN

[75] Inventor: Edwin G. Moore, Libertyville, Ill.

[73] Assignee: Abbott Laboratories, North Chicago, Ill.

[21] Appl. No.: 101,341

[22] Filed: Dec. 7, 1979

[51] Int. Cl.³ .................. G01N 33/48; C09K 3/00
[52] U.S. Cl. ............................ 252/408; 23/230 B; 23/909; 23/913; 260/112 R; 260/112 B; 356/40; 356/42; 424/2; 424/3
[58] Field of Search ........... 252/408; 23/230 B, 909, 23/913; 260/112 R, 112 B; 424/101, 2, 3; 356/40, 42

[56] References Cited

U.S. PATENT DOCUMENTS

| | | | |
|---|---|---|---|
| 3,876,375 | 9/1975 | Maurukas | 252/408 |
| 3,964,865 | 6/1976 | Das | 252/408 |
| 3,977,995 | 8/1976 | Louderback et al. | 252/408 |
| 4,200,435 | 9/1980 | Stroupe et al. | 252/408 |

OTHER PUBLICATIONS

Neer, E. J., et al., J. Bio. Chem., vol. 243, No. 8, pp. 1966–1970 and 1971–1978 (1968).
Currell, D., et al., Eur. J. Biochem., vol. 91, pp. 285–289 (1978).
Antonini, E., et al., "Hemoglobin and Myoglobin in Their Reactions with Ligands," North-Holland Publ. Co., Amsterdam, pp. 294–296 (1971).
Stevens, et al., J. Bio. Chem., vol. 252, No. 9, pp. 2998–3002 (1977).
Dolhofer, R., et al., Feas Letters, vol. 85, No. 1, pp. 86–90 (1978).
McDonald, M., et al., J. Bio. Chem., vol. 253, No. 7, pp. 2327–2332 (1978).

Primary Examiner—Teddy S. Gron
Attorney, Agent, or Firm—John J. McDonnell

[57] ABSTRACT

This invention encompasses a standard for determining glycosylated hemoglobin comprising a mixture of hemoglobin or methemoglobin and about 1% to 25% of the 2,4-dinitrophenyl derivative of hemoglobin or methemoglobin wherein a 2,4-dinitrophenyl group blocks the allosteric binding site of hemoglobin or methemoglobin.

6 Claims, No Drawings

STANDARDS FOR DETERMINING GLYCOSYLATED HEMOGLOBIN

SUMMARY OF THE INVENTION

This invention encompasses standard reagents useful in determining glycosylated hemoglobin in the blood. A mixture of hemoglobin or methemoglobin and 1% to 25% of the 2,4-dinitrophenyl derivatives of hemoglobin or methemoglobin wherein a 2,4-dinitro derivative blocks the allosteric binding site of the hemoglobin is a suitable standard. Thus, standards of the present invention mimic mixtures of glycosylated and nonglycosylated hemoglobin with respect to spectral properties associated with the R and T transformation states of hemoglobin, i.e., synthetic glycosylated hemoglobin standards. Typically standards containing 3%, 11% and 20% of the 2,4-dinitrophenyl derivative of hemoglobin or methemoglobin wherein the allosteric binding site of the hemoglobin or methemoglobin is blocked by a 2,4-dinitrophenyl group are incorporated into test kits.

BACKGROUND OF THE INVENTION

Hemoglobin exists in two allosteric forms. The T (taught) and the R (relaxed) form. These forms have different chemical and physical properties and the relative amounts of R and T hemoglobin can be determined by art recognized techniques such as ultraviolet, infrared, visible, nuclear magnetic resonance, and electron spin resonance spectroscopy. For example, Perutz, et al., *Biochemistry*, 17, 3641 (1978) describes absorption spectra of hemoglobin derivatives, i.e., R→T transition as a function of ligand and inositol hexaphosphate binding. Circular dichroism and chemical reactivity are among other techniques for distinguishing R and T states of hemoglobin. The relative amount of R and T states can be determind by both end-point and kinetic techniques.

Elevated levels of glycosylated hemoglobin are known to be associated with diabetes mellitus. Glycosylated hemoglobin is present in nondiabetics at a level of about 5% of total hemoglobin, while diabetics have 2-4 times that amount (Science, 200, Apr. 7, 1978). Glycosylated hemoglobin level provides an index of a patient's average blood glucose concentration over a long period of time. This index is not affected by short-term fluctuations in bloodsugar (hour-to-hour) and, hence, gives a relatively precise reflection of the state of blood glucose control in diabetics.

Glycosylated hemoglobin as commonly referred to as HbA, or fast hemoglobin because it migrates faster on a chromatograph column and, indeed, is generally measured by chromatography or electrophoresis.

It has recently (U.S. Ser. No. 973,368 which has a common assignee to this application) been discovered that the percent of glycosylated hemoglobin in blood can be measured by monitoring the shift in the equilibrium populations of R and T allosteric forms of hemoglobins when the nonglycosylated hemoglobin is reacted with an allosteric site binding substance. This reaction causes a shift from the R to the T allosteric form in the nonglycosylated fraction portion of the hemoglobin. The glycosylated hemoglobin in the blood sample does not contribute to the shift in the equilibrium of the allosteric forms since glycosylation blocks the allosteric binding site. Thus, the higher the percentage of glycosylated hemoglobin in the blood sample, the smaller the shift between allosteric forms upon reacting the hemoglobins with an allosteric site binding substance. The earlier discovery takes advantage of the reactivity of the allosteric binding site which is accessible in nonglycosylated hemoglobin and the resulting shift in the equilibrium of allosteric forms of the glycosylated and nonglycosylated hemoglobin mixture resulting when an allosteric binding site substance is reacted with the nonglycosylated hemoglobin fraction.

A wide variety of compounds are known as effective allosteric effector site binding substances, commonly referred to as the organophosphate binding site of hemoglobin. These include organophosphates, sulfates, carboxylic acids represented by inositol hexaphosphate, J. Biol. Chem., 246, 7168 (1971); 2,3-diphosphoglycerate, Nature, 234, 174 (1971); adenosine triphosphate, Biochem. Biophys. Res. Comm., 26, 162 (1967); pyridoxal phosphate, Fed. Proc. Fed. Amer. Soc., Expl. Biol., 28, 604 (1969); inositol pentaphosphate, Can. J. Chem., 47, 63 (1969); 8-hydroxy-1, 3,6-pyrenetrisulfonate, J. Biol. Chem., 246, 5832 (1971); 0-iodosodium benzoate, The Journal of Pharmacology and Experimental Therapeutics, 203, 72 (1977). Those skilled in the hemoglobin arts will recognize a wide variety of allosteric site binding substances. Inositol hexaphosphate is a preferred allosteric effector site binding substance.

It is generally desirable to lyse red blood cells to release hemoglobins. Common cationic (e.g., cetyl trimethyl ammonium bromide); anionic (e.g., sodium dodecylsulfate and sodium deoxycholate) and neutral (e.g., saponin and octyl phenosypolyethoxyethanol) detergents are useful in lysing red blood cells. Neutral detergents in the concentration range of about 0.025 to 0.5 volume percent are preferred. Mechanical rupture, for example, ultrasonication and hypotonic lysis, are also effective ways of releasing hemoglobin from red blood cells.

Binding of heme-binding ligands to heme iron generally shifts the equilibrium of allosteric hemoglobin isomers to the relaxed (R) form. Thus, when the heme-binding moiety of the hemoglobins in the test sample is coordinated with a heme-binding ligand larger shifts in the equilibrium populations of allosteric forms of hemoglobin are observed. This magnification in shift in equilibrium enhances accuracy and precision of glycosylated hemoglobin determination. This coordination of heme-binding ligand to shift equilibrium of allosteric isomers is applicable when the iron is in the $Fe^{+2}$ or the $Fe^{+3}$ (methemoglobin) states.

Those skilled in the hemoglobin arts will recognize a wide variety of heme-binding ligands which bind to the iron of hemoglobin or methemoglobin.

For example, isocyanides such as alkyl isocyanides having 1-6 carbon atoms or phenyl isocyanides are particularly desirable heme-binding ligands for hemoglobin in the $Fe^{+2}$ state. Other suitable ligands are $O_2$ and NO.

It is generally preferred to have a single ligand bound to iron since this results in simpler measurements of the shift in allosteric forms. For example, oxyhemoglobin (glycosylated and nonglycosylated) is preferably deoxygenated by reaction with sodium dithionite or other well-known reducing agents to deoxyhemoglobin. The deoxyhemoglobin is reacted with alkylisocyanide such as n-butylisocyanide and as a result reaction with an allosteric effector site binding ligand provides a more definitive shift in equilibrium of the allosteric forms permitting determination of glycosylated hemoglobin.

Hemoglobin is oxidized to methemoglobin by art recognized techniques, Antonini and Brunoni, *Hemoglobin and Myoglobin in Their Reaction With Ligands*, North Holland Publishing Co., Amsterdam (1971). Thus, potassium ferricyanide, sodium nitrite, aniline, and phenylhydrazine are convenient reagents for oxidizing hemoglobin to methemoglobin. Autooxidation in the presence of dyes such as methylene blue also oxidizes hemoglobin to methemoglobin.

Nonglycosylated methemoglobin is reactive with allosteric effector site binding substances described for nonglycosylated hemoglobin.

Those skilled in the hemoglobin arts will recognize a large variety of heme-binding ligands which bind with methemoglobin. These ligands include cyanate, thiocyanate, N-hydroxyacetamide, imidazole and derivatives thereof. Perutz, et al., Biochemistry, 17, 3640–3652 (1978).

Other common ligands are fluoride, azide, nitrite, cyanide, water, hydroxide ammonia, acetate and formate. Imidazole at about 0.1 M is a preferred heme-binding ligand for use with methemoglobin.

Typically, 1 ml of a reagent which is 0.1 M imidazole, 0.2 mM potassium ferricyanide, $K_3Fe(CN)_6$, and 0.05% by volume triton X-100 (octyl phenoxypolyethoxyethanol) detergent in buffer at pH 6.8 is added to 10–20 $\mu$l of whole blood and the mixture is incubated for ten minutes.

The potassium ferricyanide oxidizes the hemoglobin to methemoglobin; the triton X-100 is a neutral detergent which lyses the cells to release hemoglobins; and the imidazole coordinates with the iron shifting equilibrium allosteric isomers to the (R) form.

The absorption spectrum of this mixture is recorded at 560 nm and 635 nm. Then 2 $\mu$l of a 0.1 M inositol hexaphosphate solution, pH 6.8 is added. The latter reagent reacts with the allosteric binding site of non-glycosylated hemoglobin and shifts equilibrium of the allosteric isomers to the (T) target form. The absorption spectrum at 560 nm and 635 nm is measured again. Glycosylated hemoglobin concentration is reflected by a decrease in 560 nm absorption and increased in the 635 nm absorption.

Reagent A: 0.1 M imidazole, 0.2 mM $K_3Fe(CN)_6$, 0.05% v/v triton X-100 (octyl phenoxypolyethoxyethanol detergent), in water, pH 6.8

Reagent B: 0.1 M inositol hexaphosphate (IHP), in water, pH 6.8

To 1.0 ml of Reagent A at 25° C. add 10–20 $\mu$l whole blood, incubate 10 minutes to allow for cell lysis and oxidation of hemoglobin to methemoglobin. Record visible spectrum, 450 nm to 700 nm, specifically monitoring absorbance at 560 nm and 635 nm. Then add 2 $\mu$l Reagent B to the reaction mixture. Record another spectrum as before.

Standards prepared by methods of this invention are used to determine glycosylated hemoglobin present.

RESULTS
Standard Curve

| % Glycosylated Hb | No IHP $A^{560nm}$ | $A^{635nm}$ | + IHP $A^{560nm}$ | $A^{635nm}$ | Normalized Difference $\dfrac{\Delta\Delta}{\Delta-IHP}$ |
|---|---|---|---|---|---|
| 0% | 0.664 | 0.089 | 0.592 | 0.123 | 0.184 |
| 5% | 0.654 | 0.086 | 0.588 | 0.120 | 0.176 |
| 10% | 0.657 | 0.089 | 0.593 | 0.121 | 0.169 |
| 15% | 0.658 | 0.090 | 0.596 | 0.118 | 0.158 |
| 20% | 0.663 | 0.095 | 0.609 | 0.123 | 0.144 |
| 25% | 0.651 | 0.091 | 0.600 | 0.117 | 0.138 |
| 50% | 0.645 | 0.098 | 0.611 | 0.113 | 0.090 |
| 100% | 0.717 | 0.123 | 0.715 | 0.128 | 0.012 |

Calculations: $\Delta = A^{560nm} - A^{635nm}$

Normalized Difference $\pm$ IHP $= \dfrac{\Delta\Delta}{\Delta-IHP} = \dfrac{\Delta^{-IHP} - \Delta^{+IHP}}{\Delta-IHP}$

DETAILED DESCRIPTION OF THE INVENTION

Hemoglobin or methemoglobin is reacted with halo 2,4-dinitrobenzene wherein the halogen is chloro, fluoro, bromo, or iodo to form the 2,4-dinitrophenyl derivative of the hemoglobin or methemoglobin.

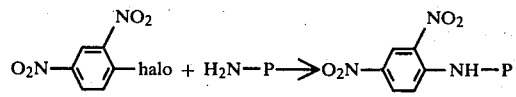

P is protein of hemoglobin or methemoglobin

Hemoglobin in cells or in solution is reacted with an excess of halo-2,4-dinitrobenzene, preferably fluoro-2,4-dinitrobenzene. In the case of initiating the process with red blood cells the cells are reacted with an excess of 2,4-dinitrobenzene, lysed, and the hemoglobin is oxidized to methemoglobin. In this process several 2,4-dinitrophenyl groups are bound to the hemoglobin and it is essential that at least one of the 2,4-dinitrophenyl groups block the allosteric binding site. In the case of initiating the process with a hemoglobin solution, the hemoglobin solution is treated with an excess of, for example, fluoro-2,4-dinitrobenzene and the derivatized product is either isolated or oxidized to methemoglobin. It is generally desirable to use methemoglobin derivative because of its stability. However, it should be pointed out that red blood cells wherein the hemoglobin has been derivatized with 2,4-dinitrophenyl group to block the allosteric binding site can be suspended in 10%–30% glycerol saline and used as standard in that form.

Although the reaction of 1-fluoro-2,4-dinitrobenzene with human hemoglobin is known *Hemoglobin and Myoglobin In Their Reaction With Ligands*, E. Antonini and M. Brunoni, North Holland Publishing Company, Amsterdam, London, 1971, pp. 295–296, 2,4-dinitrophenyl derivative of methemoglobin wherein a 2,4-dinitrophenyl group blocks the allosteric binding site of the methemoglobin is not known, nor are standard mixtures or solution of the 2,4-dinitrophenyl derivative of hemoglobin or methemoglobin wherein a 2,4-dinitrophenyl group blocks the allosteric binding site of the hemoglobin or methemoglobin known.

The 2,4-dinitrophenyl derivative of methemoglobin is a particularly preferred derivative because of its stability. Mixtures of methemoglobin and 1% to 25% of the 2,4-dinitrophenyl derivative of methemoglobin wherein a 2,4-dinitrophenyl group blocks the allosteric binding site of methemoglobin is a standard reagent particularly useful for determining glycosylated hemoglobin.

In a preferred embodiment for use in test kits, mixtures of methemoglobin and 3%, 11%, and 20% of the 2,4-dinitrophenyl derivative of methemoglobin wherein the 2,4-dinitrophenyl group blocks the allosteric binding site of methemoglobin in a 5-15 millimolar solution of protein in a phosphate buffer pH 6-8 or water solution is used.

The mixture may also be used as a lyophilized standard mixture.

The standard reagents of this invention are used in place of mixtures of hemoglobin and glycosylated hemoglobin. Glycosylated hemoglobin must be separated from blood or prepared by enzymatic reaction of glycose and hemoglobin. Reagents and standards of this invention are synthetic derivatives of hemoglobin or methemoglobin which are conveniently prepared and serve as stable standards for glycosylated hemoglobin determination.

The hereinafter set out examples are intended to illustrate the invention and are not intended to limit the invention in spirit or scope.

EXAMPLE 1

Three liters of human whole blood are stirred for 10-15 minutes and divided into six aliquot samples each of which is placed in a centrifuged tube and centrifuged at 1800 to 2000 xg for thirty minutes at 25° C. The supernatant is aspirated and 300 ml of normal saline is added to each tube and the cells are resuspended by gentle stirring. The centrifugation, aspiration and resuspension is repeated three times. The cells are then suspended in 250 ml of phosphate buffered saline pH 7.2. The suspensions are combined and to this suspension is added 15 ml of 1-fluoro-2,4-dinitrobenzene and the reaction mixture is incubated at approximately 25° C. for two hours. The suspension reacted with 1-fluoro-2,4-dinitrobenzene is again subdivided into six fractions and centrifuged at 1800-2000 xg for 15 minutes. The supernatant is decanted and discarded and the cells are lysed with water for about 1 hour at 25° C. or overnight at 4°. The tubes are centrifuged 15,000-17,000 xg for 30 minutes and the supernatant retained and stored at 2° to 8° C. The hemoglobin derivative in the supernatant is oxidized to methemoglobin by treatment with 11.0 grams of potassium ferricyanide.

The 2,4-dinitrophenyl derivative of methemoglobin is isolated on a mixed bed ion exchange resin and 1/20 volumes of 1 molar potassium phosphate, pH 6.2 is added. This solution is concentrated by dialysis on an Amicon hollow fiber dialyzer/concentrator apparatus.

The 2,4-dinitrophenyl derivative of methemoglobin is mixed with methemoglobin to provide standards ranging from 1% to 25% 2,4-dinitrophenyl derivative of methemoglobin. Standards having 5-15 millimolar protein content in phosphate buffer pH 6.8 wherein the 2,4-dinitrophenyl derivative of methemoglobin is in 3%, 11%, or 20% concentration.

EXAMPLE 2

The 2,4-dinitrophenyl derivative of hemoglobin is prepared according to the methods of Example 1 except the oxidation step with potassium ferricyanide is omitted.

EXAMPLE 3

Derivatives produced in Example 1 and 2 are produced by initiating the process with a hemoglobin solution in place of red blood cells or lysing the red blood cells prior to derivatization.

EXAMPLE 4

Following the procedure of Example 1 wherein the hemoglobin in the red blood cells is derivatized with 1-fluoro-2,4-dinitrobenzene and the red blood cells are not lysed but are combined with unreacted red blood cells, washed and stored in 10%-30% glycerol/saline to provide a stable standard. Thus, an aqueous suspension of red blood cells wherein 1% to 25% of the red blood cells have hemoglobin derivatized to form 2,4-dinitrophenyl hemoglobin wherein a 2,4-dinitrophenyl group blocks the allosteric binding site of the hemoglobin. Typically, suspensions of 3%, 11%, and 20% in 10%-30% glycerol and saline solution are incorporated into test kits.

I claim:

1. A standard for determining glycosylated hemoglobin comprising a mixture of hemoglobin and 1% to 25% of the 2,4-dinitrophenyl derivative of hemoglobin wherein a 2,4-dinitrophenyl group blocks the allosteric binding site in hemoglobin.

2. A standard, according to claim 1, wherein the mixture is in the range of 5 to 15 millimolar concentration aqueous solution.

3. A standard for determining glycosylated hemoglobin comprising a mixture of methemoglobin and 1% to 25% of 2,4-dinitrophenyl derivative of methemoglobin wherein a 2,4-dinitrophenyl group blocks the allosteric binding site of methemoglobin.

4. A standard, according to claim 3, wherein the mixture is in the range of 5 to 15 millimolar concentration in aqueous solution.

5. A standard for determining glycosylated hemoglobin comprising a suspension of red blood cells wherein 1% to 25% of red blood cells have hemoglobin derivatized to form 2,4-dinitrophenyl hemoglobin wherein a 2,4-dinitrophenyl group blocks the allosteric binding site of the hemoglobin.

6. A standard, according to claim 5, wherein the suspension is a 10%-30% glycerol in saline solution.

* * * * *